United States Patent
Jeon

(10) Patent No.: US 12,048,730 B2
(45) Date of Patent: Jul. 30, 2024

(54) PHARMACEUTICAL COMPOSITION FOR PREVENTING OR TREATING CANCER, CONTAINING OLIGOPEPTIDE AS ACTIVE INGREDIENT

(71) Applicant: L-BASE CO., LTD., Seoul (KR)

(72) Inventor: Do Yong Jeon, Seoul (KR)

(73) Assignee: L-BASE CO., LTD., Seoul (KR)

(*) Notice: Subject to any disclaimer, the term of this patent is extended or adjusted under 35 U.S.C. 154(b) by 636 days.

(21) Appl. No.: 17/413,295

(22) PCT Filed: Dec. 13, 2019

(86) PCT No.: PCT/KR2019/017650
§ 371 (c)(1),
(2) Date: Jun. 11, 2021

(87) PCT Pub. No.: WO2020/122655
PCT Pub. Date: Jun. 18, 2020

(65) Prior Publication Data
US 2022/0023378 A1    Jan. 27, 2022

(30) Foreign Application Priority Data

Dec. 13, 2018  (KR) .................. 10-2018-0160826
Dec. 12, 2019  (KR) .................. 10-2019-0165789

(51) Int. Cl.
*A61K 38/08* (2019.01)
*A61P 35/00* (2006.01)

(52) U.S. Cl.
CPC .............. *A61K 38/08* (2013.01); *A61P 35/00* (2018.01)

(58) Field of Classification Search
CPC .... A61K 38/08; A61K 38/00; A61K 38/1709; A61K 39/001184; A61P 35/00; C07K 7/06
See application file for complete search history.

(56) References Cited

U.S. PATENT DOCUMENTS

2003/0092083 A1* 5/2003 Jeoung .................. C07K 14/47
                                                435/69.3
2018/0085422 A1    3/2018 Jeoung et al.

FOREIGN PATENT DOCUMENTS

| CN | 105061562 B | 1/2018 | |
| JP | 2010-526090 A | 7/2010 | |
| KR | 10-2015-0083195 A | 7/2015 | |
| KR | 10-1848518 B1 | 4/2018 | |
| WO | 03/018629 A1 | 3/2003 | |
| WO | WO-03018629 A1 * | 3/2003 | ............. C07K 14/47 |

OTHER PUBLICATIONS

Cho et al., "Identification and Characterization of a Novel Cancer/Testis Antigen Gene CAGE", Biochem. Biophys. Res. Commun, 2002, vol. 292, pp. 715-726.
Copy of the Japanese Office Action for corresponding JP 2021-533445 mailed Nov. 28, 2023, 8 pages, with translation.
Huang et al., "Parallelization of a local similarity algorithm", CABIOS, 1992, vol. 8, No. 2, pp. 155-165.
Merrifield, "Solid Phase Peptide Synthesis. I. The Synthesis of a Tetrapeptide", J. Amer. Chem. Soc., 1963, vol. 85; pp. 2149-2154.
Pearson, "Using the FASTA Program to Search Protein and DNA Sequence Databases", Meth. Mol. Biol., 1994, vol. 24, pp. 307-331.
EESR dated Jun. 21, 2022 for the corresponding European Patent Application No. 19896436.3, 8 pages.

* cited by examiner

*Primary Examiner* — Sudhakar Katakam
(74) *Attorney, Agent, or Firm* — Vorys, Sater, Seymour and Pease LLP; Mih Suhn Koh

(57) ABSTRACT

Provided is a pharmaceutical composition for preventing or treating cancer, containing, as an active ingredient, an oligopeptide usable in treating cancer. Since an oligopeptide of the presently claimed subject matter has a molecular weight lower than those of antibodies, there are advantages for less concern of an immune response and easily penetrating into tissues, and selectively acting on cancer cells or cancer tissues.

11 Claims, 4 Drawing Sheets
Specification includes a Sequence Listing.

PHARMACEUTICAL COMPOSITION FOR PREVENTING OR TREATING CANCER, CONTAINING OLIGOPEPTIDE AS ACTIVE INGREDIENT

CROSS-REFERENCE TO RELATED APPLICATIONS

This application is a 371 of PCT/KR2019/017650 filed Dec. 13, 2019, which claims the benefit of priority from Korean Patent Application No. 10-2018-0160826 filed Dec. 13, 2018 and Korean Patent Application No. 10-2019-0165789 filed Dec. 12, 2019, the contents of each of which are incorporated herein by reference in its entirety.

SEQUENCE LISTING

The Sequence Listing submitted in text format (.txt) filed on Jun. 11, 2021, named "SequenceListing.txt", created on Jun. 11, 2021 (3.32 KB), is incorporated herein by reference.

TECHNICAL FIELD

The present invention is related to a pharmaceutical composition for preventing or treating cancer, which contains an oligopeptide that can be used to treat cancer as an active ingredient.

This application claims priority to and the benefits of Korean Patent Application No. 10-2018-0160826, filed on Dec. 13, 2018, and Korean Patent Application No. 10-2019-0165789, filed on Dec. 12, 2019, the disclosures of which are incorporated herein by reference in their entirety.

BACKGROUND ART

Although the therapeutic effect on cancer has been improved due to the development of a current diagnostic method to early detect cancer and the continuous development of a novel anticancer therapy, cancer is still an important disease that ranks as the first or second cause of death in Korea. Most of the currently used anticancer agents is chemotherapy, and have various pharmacological actions depending on the type of cancer and various side effects caused by toxicity, which leads to problems in cancer treatment.

Since existing anticancer agents penetrate not only cancer cells, but also normal tissue and thus damage the functions and activities of normal cells, they have medical problems in cancer treatment such side effects as bone marrow dysfunction, gastrointestinal disorders and hair loss, and in multi-drug resistance against long-term chemotherapy. Therefore, researches on the development of innovative anticancer drugs that can solve serious problems of conventional anticancer drugs are being actively conducted.

Meanwhile, antibodies targeting tumor cell-specific tumor antigens are being developed, but there are concerns about immune responses and low efficiency of penetration into tissue. On the other hand, unlike antibodies, since peptides have smaller molecular weights than those of antibodies, there are few concerns about immune responses, and advantages of easy penetration into tissue, and anticancer agents based on peptides targeting tumor antigens may selectively act on tumors. Thus it is expected that there will be almost no side effects such as damaging as normal cells in peptide-based anticancer drugs.

DISCLOSURE

Technical Problem

Therefore, the inventors confirmed that oligopeptides of the present invention inhibit the proliferation of cancer cells and induce apoptosis, thereby effectively treating cancer, and thus the present invention was completed.

Accordingly, the present invention is directed to providing a pharmaceutical composition for preventing or treating cancer, which includes an oligopeptide having an amino acid sequence represented by one of SEQ ID NOs: 1 to 9 as an active ingredient.

However, technical problems to be solved by the present invention are not limited to the above-described problems, and other problems which are not described herein will be fully understood by those of ordinary skill in the art from the following descriptions.

Technical Solution

To attain the above-described objects of the present invention, the present invention provides a pharmaceutical composition for preventing or treating cancer, which includes an oligopeptide having an amino acid sequence represented by one of SEQ ID NOs: 1 to 9 as an active ingredient.

In addition, the present invention provides a method of preventing or treating cancer, which includes administering an oligopeptide having an amino acid sequence represented by one of SEQ ID NOs: 1 to 9 into a subject in need of treatment.

Moreover, the present invention provides a use of an oligopeptide having an amino acid sequence represented by one of SEQ ID NOs: 1 to 9 for preventing, alleviating or treating cancer.

Further, the present invention provides a use of an oligopeptide having an amino acid sequence represented by one of SEQ ID NOs: 1 to 9 for preparing a preparation for preventing or treating cancer.

In one embodiment of the present invention, the cancer may be cancer selected from the group consisting of lung cancer, breast cancer, blood cancer and a combination thereof, but the present invention is not limited thereto.

In another embodiment of the present invention, the blood cancer may be blood cancer selected from the group consisting of leukemia, lymphoma, multiple myeloma and a combination thereof, but the present invention is not limited thereto.

In still another embodiment of the present invention, the active ingredient may be an oligopeptide having an amino acid sequence represented by one of SEQ ID NOs: 1 to 9, and the cancer may be lung cancer, but the present invention is not limited thereto.

In yet another embodiment of the present invention, the active ingredient may be an oligopeptide having an amino acid sequence represented by one of SEQ ID NOs: 6 to 9, and the cancer may be lung cancer, but the present invention is not limited thereto.

In yet another embodiment of the present invention, the active ingredient may be an oligopeptide having an amino acid sequence represented by SEQ ID NO: 6, and the cancer may be lung cancer, but the present invention is not limited thereto.

In yet another embodiment of the present invention, the active ingredient may be an oligopeptide having an amino acid sequence represented by one of SEQ ID NOs: 2 to 5, 7 and 8, and the cancer may be breast cancer, but the present invention is not limited thereto.

In yet another embodiment of the present invention, the active ingredient may be an oligopeptide having an amino acid sequence represented by one of SEQ ID NOs: 3 to 5, 7 and 8, and the cancer may be breast cancer, but the present invention is not limited thereto.

In yet another embodiment of the present invention, the active ingredient may be an oligopeptide having an amino acid sequence represented by SEQ ID NO: 7 or 3, and the cancer may be breast cancer, but the present invention is not limited thereto.

In yet another embodiment of the present invention, the active ingredient may be an oligopeptide having an amino acid sequence represented by one of SEQ ID NOs: 1 to 8, and the cancer may be blood cancer, but the present invention is not limited thereto.

In yet another embodiment of the present invention, the active ingredient may be an oligopeptide having an amino acid sequence represented by one of SEQ ID NOs: 1 to 3, 5 and 8, and the cancer may be blood cancer, but the present invention is not limited thereto.

In yet another embodiment of the present invention, the active ingredient may be an oligopeptide having an amino acid sequence represented by SEQ ID NO: 5 or 8, and the cancer may be blood cancer, but the present invention is not limited thereto.

In yet another embodiment of the present invention, the oligopeptide may inhibit PD-L1 expression, but the present invention is not limited thereto.

In yet another embodiment of the present invention, the oligopeptide may increase the expression of a gene selected from the group consisting of Bax, Bcl-x, p53 and a combination thereof, but the present invention is not limited thereto.

Advantageous Effects

Since a pharmaceutical composition according to the present invention inhibits the proliferation of cancer cells and exhibits an effect of inducing apoptosis, it can be used as an anticancer agent which is suitable for treating cancer. The pharmaceutical composition of the present invention includes an oligopeptide as an active ingredient, wherein the oligopeptide has a smaller molecular weight than an antibody and thus there are few concerns about an immune response and there is advantage that penetration into tissue is facilitated. In addition, as the pharmaceutical composition can selectively act on cancer cells or cancer tissue, it is expected to effectively improve the side effects of conventional anticancer agents.

MODES OF THE INVENTION

Figure 1:
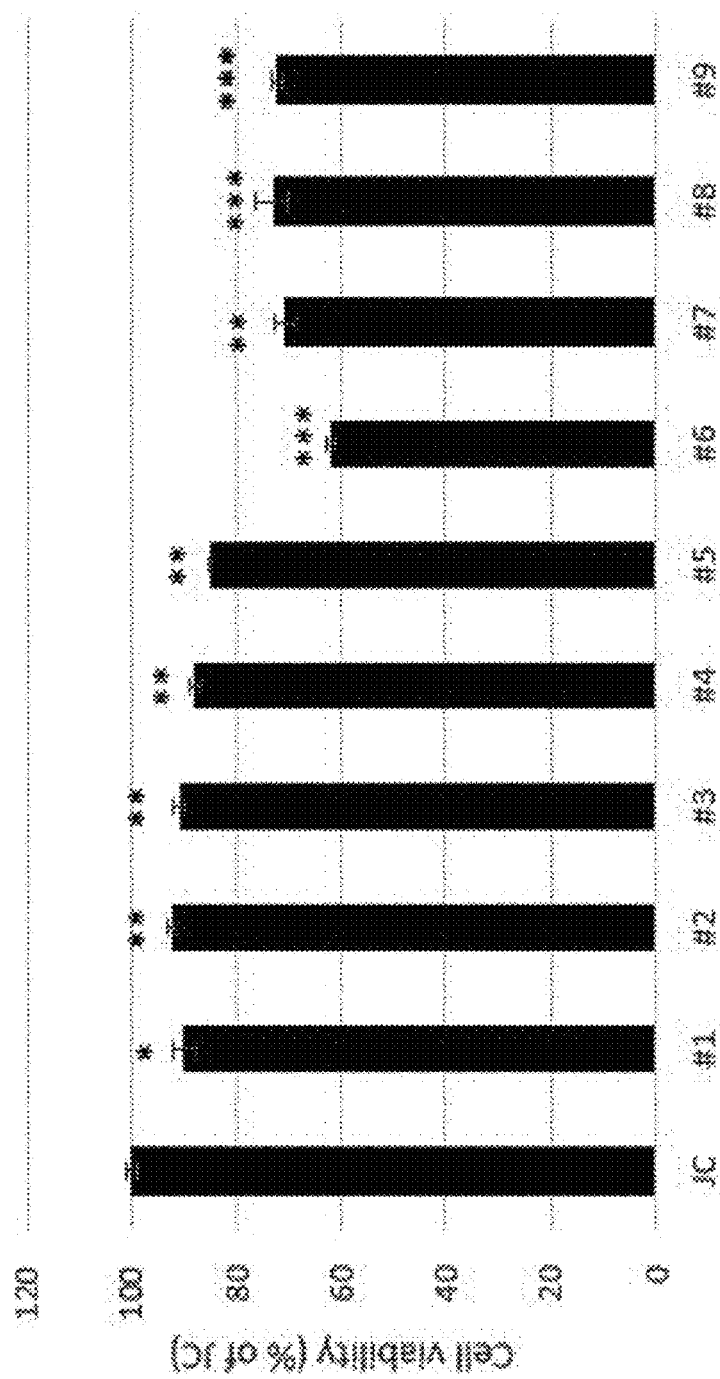
FIG. 1 is a graph showing the inhibition of the proliferation of a lung cancer cell line by an oligopeptide according to the present invention (JC: untreated control, *p<0.05, *p<0.01, and **p<0.001).

The present invention provides a pharmaceutical composition for preventing or treating cancer, which includes an oligopeptide having an amino acid sequence represented by one of SEQ ID NOs: 1 to 9 as an active ingredient.

In another aspect of the present invention, the present invention provides a method of preventing or treating cancer, which includes administering an oligopeptide having an amino acid sequence represented by one of SEQ ID NOs: 1 to 9 into a subject in need of treatment.

In still another aspect of the present invention, the present invention provides a use of an oligopeptide having an amino acid sequence represented by one of SEQ ID NOs: 1 to 9 for preventing, alleviating or treating cancer.

In yet another aspect of the present invention, the present invention provides a use of an oligopeptide having an amino acid sequence represented by one of SEQ ID NOs: 1 to 9 for preparing a preparation for preventing or treating cancer.

The term "prevention" used herein refers to all actions of preventing, inhibiting or delaying the symptoms of cancer by the administration of the composition according to the present invention.

The term "treatment" used herein refers to all actions involved in alleviating or beneficially changing the symptoms of cancer by the administration of the pharmaceutical composition according to the present invention.

The term "subject" used herein refers to a target in need of prevention or treatment of a disease. For example, the subject may be a mammal such as a human, a non-human primate, a mouse, a rat, a dog, a cat, a horse, sheep or a cow.

The term "oligopeptide" used herein refers to a linear molecule formed by amino acid residues connected by peptide bonds. The oligopeptide of the present invention may be prepared by a chemical synthesis method (e.g., a solid-phase synthesis techniques) known in the art along with a molecular biology method (Merrifield, *J Amer. Chem. Soc.* 85: 2149-54 (1963): Stewart, et al., Solid Phase Peptide Synthesis, 2nd. ed., Pierce Chem. Co.: Rockford, 111 (1984)).

The range of the oligopeptide of the present invention may include a pharmaceutically acceptable salt thereof. The term "pharmaceutically acceptable" used herein refers to an oligopeptide which is suitable to be used in contact with tissue of a subject (e.g., a human) since there is a reasonable benefit/risk ratio without excessive toxicity, irritation, allergic reactions, other problems or complications, and within the scope of sound medical judgment. The pharmaceutically acceptable salt includes, for example, an acid addition salt formed by a pharmaceutically acceptable free acid and a pharmaceutically acceptable metal salt.

In addition, the range of the oligopeptide of the present invention may include a biologically functional equivalent having a modification in the amino acid sequence exhibiting biological activity equivalent to that of the oligopeptide in the present invention. The modification in the amino acid sequence may be made based on the relative similarities of amino acid side chain substituents, for example, hydrophobicity, hydrophilicity, charge and a size. According to the analyses of the size, shape and type of an amino acid side chain substituent, it can be seen that all of arginine, lysine and histidine are positively-charged residues; alanine, glycine and serine have similar sizes; and phenylalanine, tryptophan and tyrosine have similar shapes. Therefore, based on these considerations, arginine, lysine and histidine; alanine, glycine and serine; and phenylalanine, tryptophan and tyrosine may be biologically functional equivalents.

To introduce modifications, a hydrophobicity index of an amino acid may be considered. Each amino acid has a hydrophobicity index according to its hydrophobicity and charge. In addition, it is also known that substitution between amino acids having similar hydrophilicity values leads to peptides with equivalent biological activity.

Amino acid exchanges in peptides that do not totally change the activity of a molecule are known in the art (H. Neurath, R. L. Hill, The Proteins, Academic Press, New York, 1979). The most common exchanges are exchanges between amino acid residues such as Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn. Leu/Ile, Leu/Val, Ala/Glu, and Asp/Gly.

Considering the above-described modifications having biologically equivalent activity, it is interpreted that the oligopeptide of the present invention also includes a sequence having substantial identity with a sequence disclosed in the sequence listing. The substantial identity may mean a sequence showing at least 80%, 90% or 95% homology when the sequence of the present invention and another sequence are aligned to correspond as much as possible, and the aligned sequence is analyzed using an algorithm commonly used in the art. Alignment methods for sequence comparison are known in the art (Huang et al., *Comp. Appl. BioSci.* 8:155-65 (1992); Pearson et al., *Meth. Mol. Biol.* 24:307-31 (1994)).

The pharmaceutical composition of the present invention is used in prevention or treatment of cancer. Cancer for which the pharmaceutical composition of the present invention is used may be cancer selected from the group consisting of lung cancer, breast cancer, blood cancer and a combination thereof, but the present invention is not limited thereto.

In the present invention, the blood cancer may be blood cancer selected from the group consisting of leukemia, lymphoma, multiple myeloma and a combination thereof, but the present invention is not limited thereto.

In one embodiment of the present invention, it was confirmed that the oligopeptides of the present invention exhibit excellent anticancer activity against lung cancer, breast cancer and blood cancer (see Example 2).

In the present invention, when the pharmaceutical composition is used in prevention or treatment of lung cancer, the composition may include the following oligopeptide as an active ingredient, but the present invention is not limited thereto:

(i) an oligopeptide having an amino acid sequence represented by one of SEQ ID NOs: 1 to 9;

(ii) an oligopeptide having an amino acid sequence represented by one of SEQ ID NOs: 6 to 9; or (iii) an oligopeptide having an amino acid sequence represented by SEQ ID NO: 6.

In addition, in the present invention, when the pharmaceutical composition is used in prevention or treatment of breast cancer, the composition may include the following oligopeptide as an active ingredient, but the present invention is not limited thereto:

(i) an oligopeptide having an amino acid sequence represented by one of SEQ ID NOs: 2 to 5, 7 and 8:

(ii) an oligopeptide having an amino acid sequence represented by one of SEQ ID NOs: 3 to 5, 7 and 8; or (iii) an oligopeptide having an amino acid sequence represented by one of SEQ ID NO: 7 or 3.

In addition, in the present invention, when the pharmaceutical composition is used in prevention or treatment of blood cancer, the composition may include the following oligopeptide as an active ingredient, but the present invention is not limited thereto:

(i) an oligopeptide having an amino acid sequence represented by one of SEQ ID NOs: 1 to 8;

(ii) an oligopeptide having an amino acid sequence represented by one of SEQ ID NOs: 1 to 3, 5 and 8; or (iii) an oligopeptide having an amino acid sequence represented by one of SEQ ID NO: 5 or 8.

In the present invention, the oligopeptide may inhibit PD-L1 expression, but the present invention is not limited thereto.

In the present invention, the oligopeptide may increase the expression of a gene selected from the group consisting of Bax, Bcl-x, p53 and a combination thereof, but the present invention is not limited thereto.

In one embodiment of the present invention, as a result of measuring the changes in expression of genes (PD-L1, Bax, Bcl-x and p53) related to apoptosis in cancer cells by the oligopeptide of the present invention, the expression of PD-L1 was inhibited and the expression of the Bax, Bcl-x and p53 genes increased (see Example 3). It is known that the PD-L1 is a protein present on the surface of a cancer cell, and binds with PD-1, which is a surface protein of a T cell, to interfere with the T cell attack on cancer cells, and the Bcl-2-associated X (Bax) protein is a protein inducing apoptosis, whose expression is regulated by p53, which is a tumor suppressor. In addition, B-cell lymphoma-X (Bcl-X) is known as an apoptosis regulator inducing apoptosis according to morphology. Accordingly, the result of the embodiment shows that the oligopeptide of the present invention may increase T cell sensitivity for cancer cells, and induce the apoptosis of cancer cells.

Meanwhile, the pharmaceutical composition according to the present invention may further include a suitable carrier, excipient and/or diluent conventionally used to prepare a pharmaceutical composition in addition to the active ingredient. In addition, the pharmaceutical composition according to the present invention may be formulated into an oral formulation such as a powder, a granule, a tablet, a capsule, a suspension, an emulsion, a syrup or an aerosol, a preparation for external use, a suppository and a sterile injectable solution according to conventional methods.

As a carrier, excipient and diluent, which can be included in the composition, there may be lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methylhydroxy benzoate, propylhydroxy benzoate, talc, magnesium stearate, and mineral oil. The composition may be formulated with a diluent or an excipient such as a filler, a thickening agent, a binder, a wetting agent, a disintegrant, or a surfactant, which are conventionally used.

The composition according to the present invention is administered at a pharmaceutically effective amount. In the present invention, the "pharmaceutically effective amount" used herein refers to an amount sufficient for treating a disease at a reasonable benefit/risk ratio applicable for medical treatment, and an effective dosage may be determined by parameters including a patient's disease type, severity, drug activity, sensitivity to a drug, administration time, an administration route and an excretion rate, the duration of treatment and drugs simultaneously used, and other parameters well known in the medical field. A preferable dose may be selected by the condition and body weight of a subject, the severity of a disease, a dosage form, and the route and period of administration. Specifically, the pharmaceutical composition may be administered at 0.001 to 1,000 mg/kg, 0.01 to 100 mg/kg, 0.01 to 10 mg/kg, 0.1 to 10 mg/kg or 0.1 to 1 mg/kg daily once or divided into once to several times.

In consideration of all of the above-described factors, it is important to administer a minimum amount that can obtain the maximum effect without side effects, and the amount may be determined by one of ordinary skill in the art. Specifically, the effective amount of the pharmaceutical composition according to the present invention may vary according to a patient's age, sex, condition and a body weight, the absorbance of an active ingredient into the body, an inactivation ratio, an excretion rate, the type of a disease, and a drug used in combination.

The pharmaceutical composition of the present invention may be administered into a subject in various routes. For example, the pharmaceutical composition of the present invention may be administered by oral administration, intranasal administration, transbronchial administration, arterial injection, intravenous injection, subcutaneous injection, intramuscular injection or intraperitoneal injection. The daily dose may be administered once or in divided portions.

Hereinafter, to help in understanding the present invention, exemplary examples will be suggested. However, the following examples are merely provided to more easily understand the present invention, and not to limit the present invention.

EXAMPLES

Example 1. Preparation of Oligopeptides

Oligopeptides having amino acid sequences shown in Table 1 below were synthesized. The oligopeptides were synthesized by commissioning Sewon Biotechnology Co., Ltd. and Peptron Co., Ltd, and the synthesized peptides were identified through LC-MS/MS, amino acid sequence analysis and NMR structure analysis, and a purity was determined to be 95% or more by HPLC.

TABLE 1

| Peptide | | Amino acid sequence |
|---|---|---|
| pep #1 | (SEQ ID NO: 1) | ATWPDTVRQL |
| pep #2 | (SEQ ID NO: 2) | TSATWPDTVR |
| pep #3 | (SEQ ID NO: 3) | WPDTVRQLAL |
| pep #4 | (SEQ ID NO: 4) | CSKYSYKGLK |
| pep #5 | (SEQ ID NO: 5) | AECSKYSYKG |
| pep #6 | (SEQ ID NO: 6) | QTVMTSATWP |
| pep #7 | (SEQ ID NO: 7) | SICIYGGRNR |
| pep #8 | (SEQ ID NO: 8) | GMLVLTPTRE |
| pep #9 | (SEQ ID NO: 9) | SREQRNGPGM |

Example 2. Measurement of Cancer Cell Proliferation Inhibitory Activity of Oligopeptides To measure the cancer cell proliferation inhibitory effect of the oligopeptides synthesized in Example 1, an MTS (3-(4,5-dimethylthiazol-2-y)-5-(3-carboxymethoxyphenyl)-2-(4-sulfophenyl)-2H-tetrazolium, inner salt) assay for cancer cells was performed. Specifically, each of a lung cancer cell line (H1975), a breast cancer cell line (MDA-MB-231) and a blood cancer cell line (Daudi), which were cultured in 96-well microplates, was treated with 500 μM of the oligopeptides synthesized in Example 1, and incubated in a 37° C. incubator for 72 hours. Each cell culture was treated with an MTS reagent and incubated in a 37° C. incubator for 30 minutes or more, and absorbance (OD) was measured at 490 nm. The result is shown in FIGS. 1 to 3.

As shown in FIG. 1, the proliferation of the lung cancer cell line was inhibited by oligopeptide treatment. Specifically, all oligopeptides exhibited better cancer cell proliferation inhibitory activity than an untreated control, and among the oligonucleotides, particularly, the oligopeptide pep #6, #7, #8 and #9 exhibited excellent cancer cell proliferation inhibitory effects.

Figure 2:
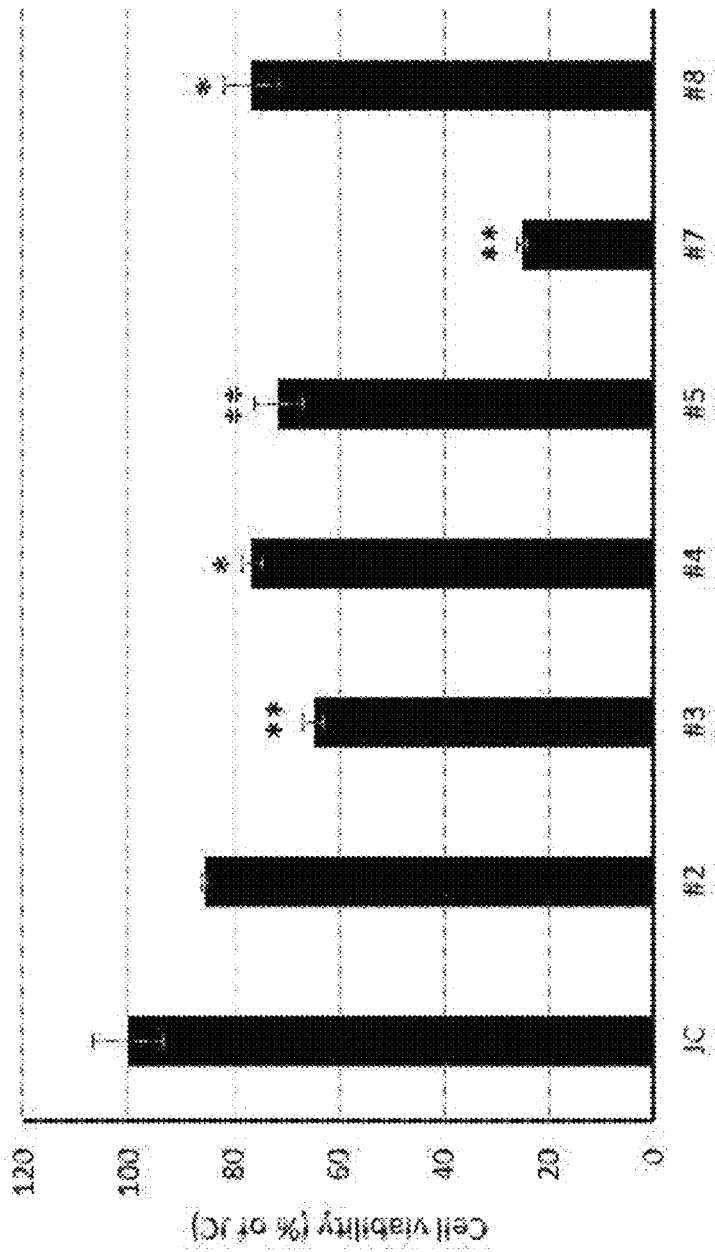
FIG. 2 is a graph showing the inhibition of the proliferation of a breast cancer cell line by an oligopeptide according to the present invention (JC: untreated control, *p<0.05, and **p<0.01).

In addition, as shown in FIG. 2, the proliferation of a breast cancer cell line was inhibited by the oligopeptide treatment. Specifically, the oligopeptide pep #7, #3, #5, #4, #8 and #2 exhibited a better cancer cell proliferation inhibitory effect than an untreated control, and among these oligopeptides, particularly, the oligopeptide pep #7, #3 and #5 exhibited excellent cancer cell proliferation inhibitory effects.

Figure 3:
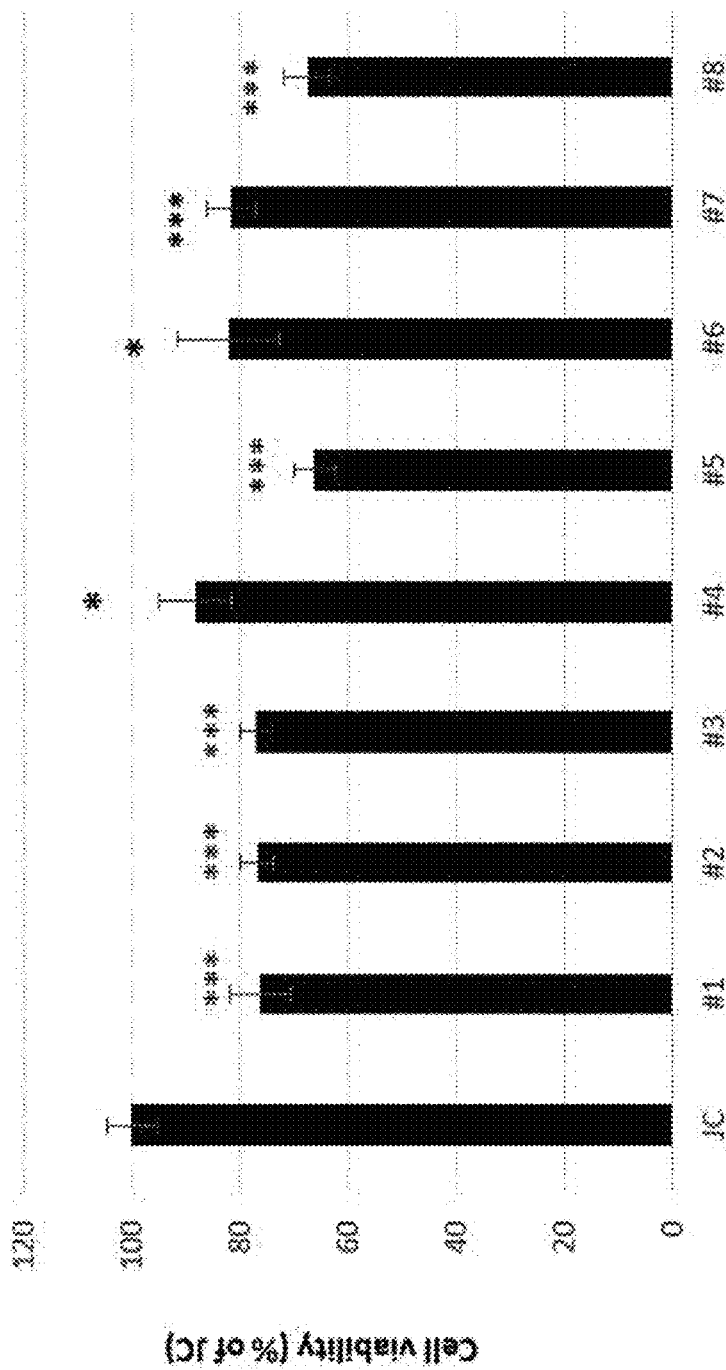
FIG. 3 is a graph showing the inhibition of the proliferation of a blood cancer cell line by an oligopeptide according to the present invention (JC: untreated control, *p<0.05, and **p<0.001).

Moreover, as shown in FIG. 3, the proliferation of a blood cancer cell line was inhibited by the oligopeptide treatment. Specifically, the oligopeptide pep #5, #8, #1, #2, #3, #7, #6 and #4 exhibited better cancer cell proliferation inhibitory activity than an untreated control, and among these oligopeptides, particularly, the oligopeptide pep #5 and #8 exhibited excellent cancer cell proliferation inhibitory activity.

Example 3. Measurement of Expression of Apoptosis-Related Genes

The expression of PD-L1, Bax, Bcl-x and p53, which are apoptosis-related genes in cancer cells, by the oligopeptides synthesized in Example 1 was measured. PD-L1 is a protein present on the surface of a cancer cell, and binds with PD-1, which is a surface protein of a T cell, to interfere with T cell attack on cancer cells. Bcl-2-associated X protein (Bax) is a protein inducing apoptosis, and regulates expression by p53, which is a tumor suppressor. B-cell lymphoma-X (Bcl-X) is an apoptosis regulator inducing apoptosis according to morphology.

Figure 4:
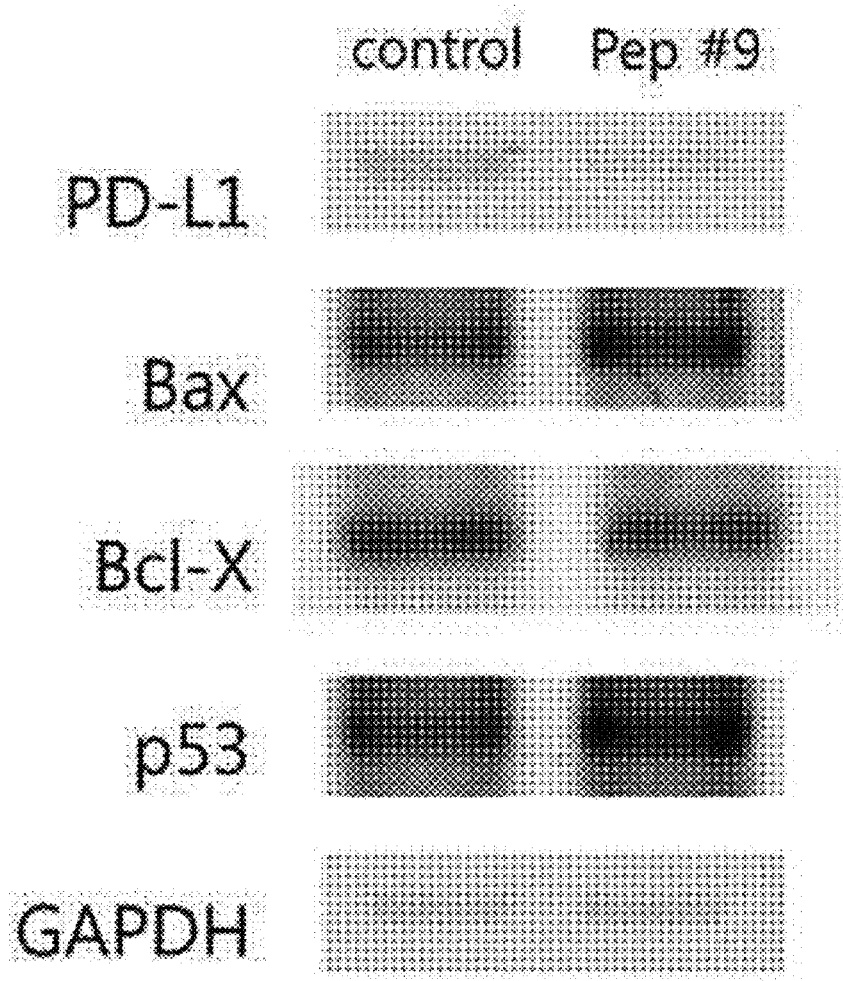
FIG. 4 are images showing the change in expression of PD-L1, Bax, Bcl-x and p53, which are genes involved in apoptosis in cancer cells, by an oligopeptide according to the present invention.

A blood cancer cell line (RPMI8226) incubated in a 6-well microplate was treated with 10 μM of the oligopeptide pep #9 synthesized in Example 1, and incubated in a 37° C. incubator for 48 hours. DNA was extracted from the cells, the expression of each gene was measured by polymerization chain reaction (PCR, reaction concentrations: at 95° C. for 5 min→95° C. for 45 sec, 56° C. for 45 sec, 72° C. for 45 sec (repeated for 35 cycles)→72° C. for 5 min) using primers shown in Table 2 below, and the result is shown in FIG. 4.

TABLE 2

| Primer | Base sequence (5' > 3') | SEQ ID NO: |
|---|---|---|
| PD-L1_F | GACCTATATGTGGTAGAGTATG GTAGC | 10 |
| PD-L1_R | TTCAGCTGTATGGTTTTCCTCA GGATC | 11 |

TABLE 2-continued

| Primer | Base sequence (5' > 3') | SEQ ID NO: |
|---|---|---|
| Bax_F | GGCCCACCAGCTCTGAGCAGA | 12 |
| Bax_R | GCCACGTGGGCGTCCCAAAGT | 13 |
| Bcl-x_F | TTGGACAATGGACTGGTTGA | 14 |
| Bcl-x_R | GTAGAGTGGATGGTCAGTG | 15 |
| p53_F | GCGTGTGGAGTATTTGGA | 16 |
| p53_R | GAGAGGAGCTGGTGTTGTT | 17 |

As shown in FIG. 4, the oligopeptides inhibited the expression of PD-L1, which is a gene in cancer cells, and increased the expression of genes Bax, Bcl-x and p53. Such results show that the oligopeptides according to the present invention increase T cell sensitivity for cancer cells, and induce the apoptosis of cancer cells.

It should be understood by those of ordinary skill in the art that the above description of the present invention is exemplary, and the exemplary embodiments disclosed herein can be easily modified into other specific forms without departing from the technical spirit or essential features of the present invention. Therefore, the exemplary embodiments described above should be interpreted as illustrative and not limited in any aspect.

INDUSTRIAL APPLICABILITY

Since a pharmaceutical composition according to the present invention may inhibit the proliferation of cancer cells, and exhibit an apoptosis-inducing effect, it may be used as an anticancer agent useful for treating cancer. The pharmaceutical composition of the present invention includes an oligopeptide as an active ingredient, wherein the oligopeptide has a smaller molecular weight than an antibody and thus there are few concerns about an immune response and there is advantage that penetration into tissue is facilitated. In addition, as the pharmaceutical composition can selectively act on cancer cells or cancer tissue, it is expected to effectively improve side effects of conventional anticancer agents.

The invention claimed is:

1. A method of treating cancer by administering an effective amount of an oligopeptide having an amino acid sequence represented by one of SEQ ID NOs: 1 to 9 into an individual in need thereof, wherein the cancer is selected from the group consisting of lung cancer, breast cancer, blood cancer and a combination thereof.

2. The method of claim 1, wherein the blood cancer is selected from the group consisting of leukemia, lymphoma, multiple myeloma and a combination thereof.

3. The method of claim 1, wherein the oligopeptide having an amino acid sequence represented by one of SEQ ID NOs: 1 to 9, and the cancer is lung cancer.

4. The method of claim 1, wherein the oligopeptide having an amino acid sequence represented by one of SEQ ID NOs: 6 to 9, and the cancer is lung cancer.

5. The method of claim 1, wherein the oligopeptide having an amino acid sequence represented by SEQ ID NO: 6, and the cancer is lung cancer.

6. The method of claim 1, wherein the oligopeptide having an amino acid sequence represented by one of SEQ ID NOs: 2 to 5, 7 and 8, and the cancer is breast cancer.

7. The method of claim 1 wherein the oligopeptide having an amino acid sequence represented by one of SEQ ID NOs: 3 to 5, 7 and 8, and the cancer is breast cancer.

8. The method of claim 1, wherein the oligopeptide having an amino acid sequence represented by SEQ ID NO: 7 or 3, and the cancer is breast cancer.

9. The method of claim 1, wherein the oligopeptide having an amino acid sequence represented by one of SEQ ID NOs: 1 to 8, and the cancer is blood cancer.

10. The method of claim 1 wherein the oligopeptide having an amino acid sequence represented by one of SEQ ID NOs: 1 to 3, 5 and 8, and the cancer is blood cancer.

11. The method of claim 1 wherein the oligopeptide having an amino acid sequence represented by SEQ ID NO: 5 or 8, and the cancer is blood cancer.

* * * * *

SEQUENCE LISTING

<160> NUMBER OF SEQ ID NOS: 17

<210> SEQ ID NO 1
<211> LENGTH: 10
<212> TYPE: PRT
<213> ORGANISM: Artificial Sequence
<220> FEATURE:
<223> OTHER INFORMATION: pep #1

<400> SEQUENCE: 1

Ala Thr Trp Pro Asp Thr Val Arg Gln Leu
1               5                   10

<210> SEQ ID NO 2
<211> LENGTH: 10
<212> TYPE: PRT
<213> ORGANISM: Artificial Sequence
<220> FEATURE:
<223> OTHER INFORMATION: pep #2

<400> SEQUENCE: 2

Thr Ser Ala Thr Trp Pro Asp Thr Val Arg
1               5                   10

<210> SEQ ID NO 3
<211> LENGTH: 10
<212> TYPE: PRT
<213> ORGANISM: Artificial Sequence
<220> FEATURE:
<223> OTHER INFORMATION: pep #3

<400> SEQUENCE: 3

Trp Pro Asp Thr Val Arg Gln Leu Ala Leu
1               5                   10

<210> SEQ ID NO 4
<211> LENGTH: 10
<212> TYPE: PRT
<213> ORGANISM: Artificial Sequence
<220> FEATURE:
<223> OTHER INFORMATION: pep #4

<400> SEQUENCE: 4

Cys Ser Lys Tyr Ser Tyr Lys Gly Leu Lys
1               5                   10

<210> SEQ ID NO 5
<211> LENGTH: 10
<212> TYPE: PRT
<213> ORGANISM: Artificial Sequence
<220> FEATURE:
<223> OTHER INFORMATION: pep #5

<400> SEQUENCE: 5

Ala Glu Cys Ser Lys Tyr Ser Tyr Lys Gly
1               5                   10

<210> SEQ ID NO 6
<211> LENGTH: 10
<212> TYPE: PRT
<213> ORGANISM: Artificial Sequence
<220> FEATURE:
<223> OTHER INFORMATION: pep #6

<400> SEQUENCE: 6

Gln Thr Val Met Thr Ser Ala Thr Trp Pro
1               5                   10

<210> SEQ ID NO 7
<211> LENGTH: 10
<212> TYPE: PRT
<213> ORGANISM: Artificial Sequence
<220> FEATURE:
<223> OTHER INFORMATION: pep #7

<400> SEQUENCE: 7

Ser Ile Cys Ile Tyr Gly Gly Arg Asn Arg
1               5                   10

<210> SEQ ID NO 8
<211> LENGTH: 10
<212> TYPE: PRT
<213> ORGANISM: Artificial Sequence
<220> FEATURE:
<223> OTHER INFORMATION: pep #8

<400> SEQUENCE: 8

Gly Met Leu Val Leu Thr Pro Thr Arg Glu
1               5                   10

<210> SEQ ID NO 9
<211> LENGTH: 10
<212> TYPE: PRT
<213> ORGANISM: Artificial Sequence
<220> FEATURE:
<223> OTHER INFORMATION: pep #9

<400> SEQUENCE: 9

Ser Arg Glu Gln Arg Asn Gly Pro Gly Met
1               5                   10

<210> SEQ ID NO 10
<211> LENGTH: 27
<212> TYPE: DNA
<213> ORGANISM: Artificial Sequence
<220> FEATURE:
<223> OTHER INFORMATION: PD-L1_F primer

<400> SEQUENCE: 10

```
gacctatatg tggtagagta tggtagc                                              27

<210> SEQ ID NO 11
<211> LENGTH: 27
<212> TYPE: DNA
<213> ORGANISM: Artificial Sequence
<220> FEATURE:
<223> OTHER INFORMATION: PD-L1_R primer

<400> SEQUENCE: 11
ttcagctgta tggttttcct caggatc                                              27

<210> SEQ ID NO 12
<211> LENGTH: 21
<212> TYPE: DNA
<213> ORGANISM: Artificial Sequence
<220> FEATURE:
<223> OTHER INFORMATION: Bax_F primer

<400> SEQUENCE: 12
ggcccaccag ctctgagcag a                                                    21

<210> SEQ ID NO 13
<211> LENGTH: 21
<212> TYPE: DNA
<213> ORGANISM: Artificial Sequence
<220> FEATURE:
<223> OTHER INFORMATION: Bax_R primer

<400> SEQUENCE: 13
gccacgtggg cgtcccaaag t                                                    21

<210> SEQ ID NO 14
<211> LENGTH: 20
<212> TYPE: DNA
<213> ORGANISM: Artificial Sequence
<220> FEATURE:
<223> OTHER INFORMATION: Bcl-x_F primer

<400> SEQUENCE: 14
ttggacaatg gactggttga                                                      20

<210> SEQ ID NO 15
<211> LENGTH: 19
<212> TYPE: DNA
<213> ORGANISM: Artificial Sequence
<220> FEATURE:
<223> OTHER INFORMATION: Bcl-x_R primer

<400> SEQUENCE: 15
gtagagtgga tggtcagtg                                                       19

<210> SEQ ID NO 16
<211> LENGTH: 18
<212> TYPE: DNA
<213> ORGANISM: Artificial Sequence
<220> FEATURE:
<223> OTHER INFORMATION: p53_F primer

<400> SEQUENCE: 16
gcgtgtggag tatttgga                                                        18

<210> SEQ ID NO 17
<211> LENGTH: 19
<212> TYPE: DNA
<213> ORGANISM: Artificial Sequence
```

```
<220> FEATURE:
<223> OTHER INFORMATION: p53_R primer

<400> SEQUENCE: 17
gagaggagct ggtgttgtt                                              19
```